United States Patent

Potti et al.

(12) United States Patent
(10) Patent No.: US 6,171,323 B1
(45) Date of Patent: Jan. 9, 2001

(54) TONGUE CLEANER

(76) Inventors: Dasan Potti, 27104 Patriot Dr., Salisbury, MD (US) 21801; Jon L. Richter, 1-104 Bleddyn Rd., Ardmore, PA (US) 19003; Gordon Neufeld, 6015 W. Valley Green Rd., Flourtown, PA (US) 19031

( * ) Notice: Under 35 U.S.C. 154(b), the term of this patent shall be extended for 243 days.

(21) Appl. No.: 08/665,835

(22) Filed: Jun. 19, 1996

(51) Int. Cl.[7] ................................................. A61B 17/24
(52) U.S. Cl. ............................................ 606/161; 600/570
(58) Field of Search ................................... 606/160, 161; 128/757; 600/570

(56) References Cited

U.S. PATENT DOCUMENTS

| D. 106,324 | 10/1937 | Nuessle et al. . |
| D. 221,036 | 6/1971 | Potti . |
| D. 276,088 | 10/1984 | Fong . |
| D. 309,040 | 7/1990 | Poon . |
| D. 316,617 | 4/1991 | Cheung . |
| D. 338,084 | 8/1993 | Potti . |
| 1,811,775 | 6/1931 | Barkwill . |
| 2,543,999 | 3/1951 | Voss . |
| 2,574,654 | 10/1951 | Moore . |
| 3,101,727 | 8/1963 | Wiseman . |
| 3,477,435 | 11/1969 | Artelli . |
| 4,911,187 | 3/1990 | Castillo . |
| 5,005,246 | * | 4/1991 | Yen-Hui ............................ 606/161 |

FOREIGN PATENT DOCUMENTS 659404   6/1929   (FR) .

* cited by examiner

*Primary Examiner*—Michael Buiz
*Assistant Examiner*—William W. Lewis
(74) *Attorney, Agent, or Firm*—Hodgson, Russ, Andrews, Woods & Goodyear LLP

(57) ABSTRACT

A tongue cleaner having an elongate shank portion for holding thereof and a portion extending from one end thereof for supporting a tongue scraping edge. The support portion is skewed relative to the shank portion to slope downwardly for effecting engagement of the edge with a posterior part of the upper surface of the tongue so that the posterior part may be comfortably scraped.

11 Claims, 2 Drawing Sheets

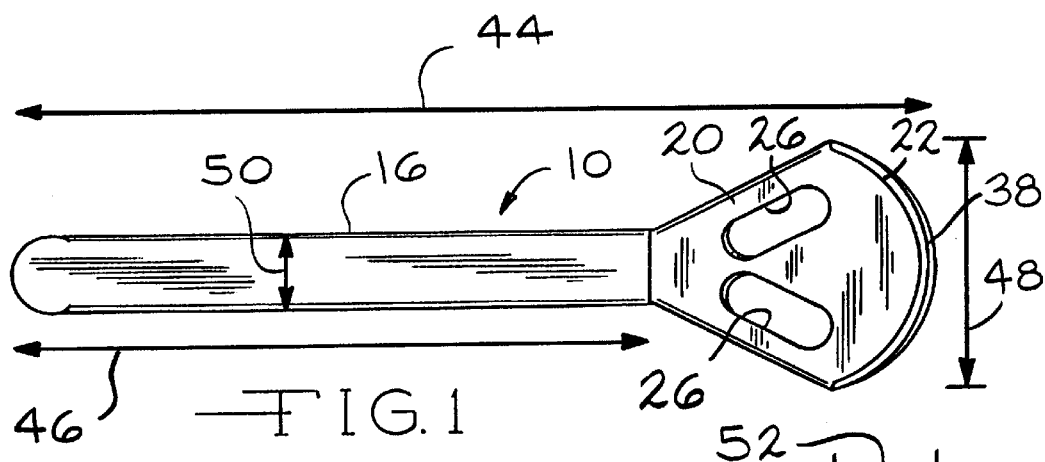
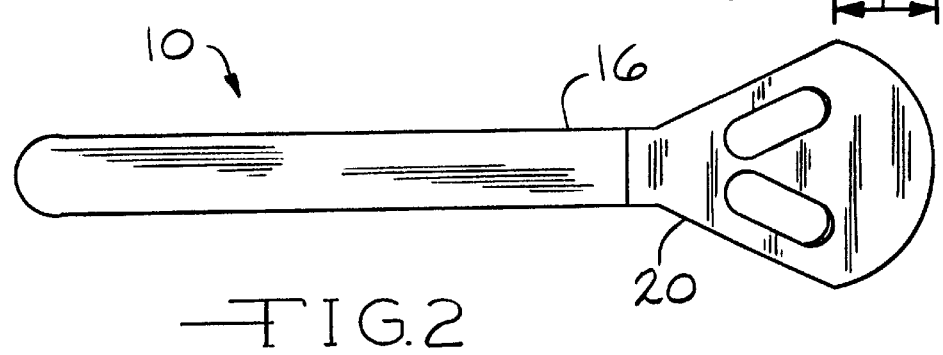
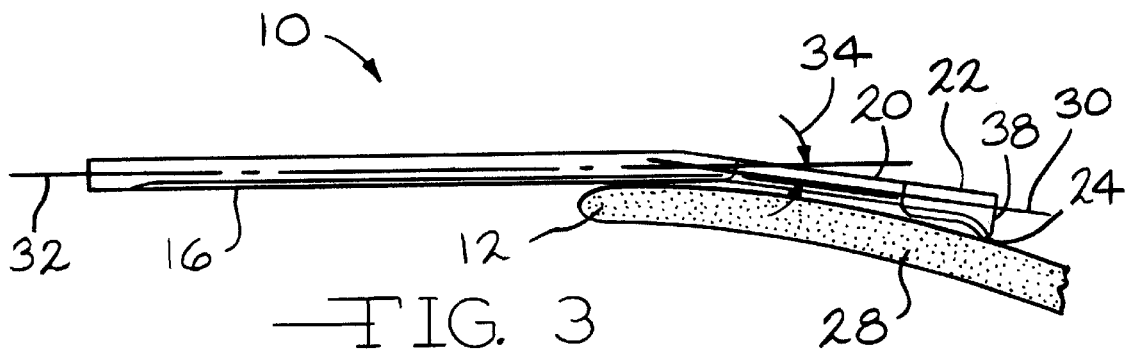
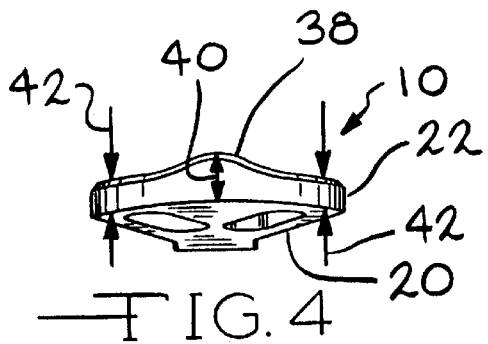
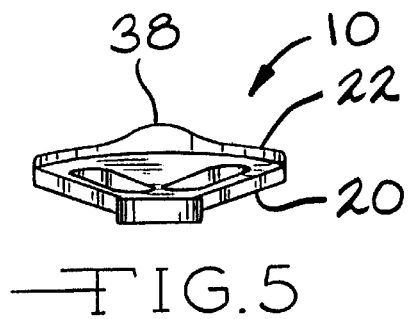

TONGUE CLEANER

The present invention relates generally to tongue cleaners, i.e., articles which are used to scrape the upper surface of a person's tongue.

Examples of tongue cleaners are found in U.S. Pat. Nos. D221,036 and D338,084, which issued to Dasan Potti, one of the applicants of the present application. At one end of the shank, a portion flares outwardly to support, at an end of the tongue cleaner, a tongue scraping edge. The edge is moved over the tongue's upper surface from rear to front perhaps 2 to 3 times firmly scraping the upper surface. Such a tongue cleaning exercise is performed, after brushing teeth, to cause the taste buds to "wake up" and halitosis to diminish. By removing growing bacteria and decaying food particles that cause plaque, tongue cleaning by use of such a device may minimize tooth decay and gum disease (gingivitis). Unlike a toothbrush, such a tongue cleaning device cleans the tongue gently and smoothly.

It is considered desirable to scrape the entire upper surface of the tongue. While the anterior portion of the tongue may be easily reached by the tongue cleaners in the above patents, the posterior part of the tongue extends or slopes downwardly so that it is not as easy for a tongue cleaner to reach this posterior portion. Thus, it may uncomfortably require the person to tilt the shank up to the roof of the mouth, which many persons may choose to ignore to do.

It is accordingly an object of the present invention to provide a tongue cleaner which allows the entire tongue including the posterior portion to be more easily cleaned.

In order that a person may be able to easily reach the posterior portion of the tongue for cleaning thereof, in accordance with the present invention, a tongue cleaner portion which supports the edge portion for scraping the tongue is skewed relative to the shank to slope downwardly, following the downward slope of the posterior portion of the tongue, for effective engagement of the edge with the posterior portion of the tongue without the user having to uncomfortably tilt the shank toward the roof of the mouth.

The above and other objects, features, and advantages of the present invention will be apparent in the following detailed description of the preferred embodiment thereof when read in conjunction with the accompanying drawings wherein the same reference numerals denote the same or similar parts throughout the several views.

BRIEF DESCRIPTION OF THE DRAWINGS

FIG. 1 is a top plan view of a tongue cleaner which embodies the present invention.

FIG. 2 is a bottom view thereof.

FIG. 3 is a side view thereof, illustrated scraping the posterior part of a person's tongue, the opposite side being identical thereto.

FIG. 4 is an end view thereof.

FIG. 5 is another end view thereof.

DETAILED DESCRIPTION OF THE PREFERRED EMBODIMENT

Figure 6:
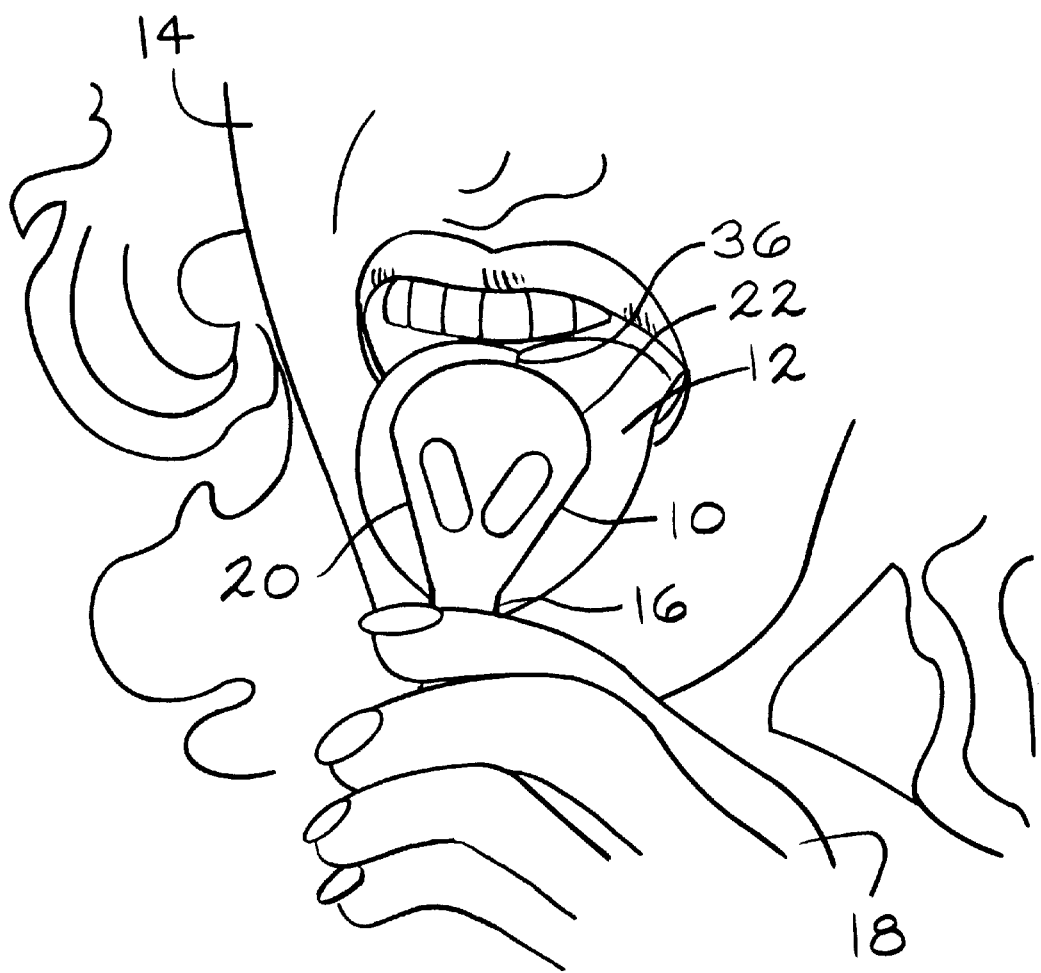
FIG. 6 is a perspective view illustrating use thereof in cleaning the tongue.

Referring to the drawings, there is shown generally at 10 a single-piece thin article, composed of molted plastic or other suitable material, for cleaning the tongue 12 of a person 14. The tongue cleaner 10 includes an elongate shank portion 16 for holding in the user's hand 18 for tongue cleaning, as hereinafter discussed. A portion 20 extends from one end of shank 16 and flares outwardly therefrom to support at an end of the tongue cleaner an edge portion 22. Thus, the sides of the support portion 20 extend outwardly from the sides of the shank so that the width, illustrated at 48, of the support portion 20 (for reaching of the tongue) is greater than the width of the shank (for easily holding in the hand 18).

The edge portion 22, which is shaped like a fender, is concave as viewed from the shank 16 and provides an arcuate edge 24 which contacts or engages the tongue 12 for scraping thereof, the edge being arcuate in order that the posterior portion of the tongue may be more easily reached without unnecessarily increasing the tongue cleaner width. A pair of oblong holes, illustrated at 26, are provided through the support portion 20 and extend parallel to the sides thereof respectively in order to provide increased flexibility.

The posterior portion, illustrated at 28, of the tongue upper surface generally extends downwardly from the anterior portion thereof, as illustrated in FIG. 3, so that it is uncomfortable to reach with a straight tongue cleaner such as shown in the aforesaid patents. In order to comfortably reach the posterior portion 28 of the tongue, in accordance with the present invention, the support portion 20 is skewed relative to the shank portion 16 to slope downwardly for effecting engagement of the edge 24 with the posterior part 28 of the tongue upper surface. Stated another way, the support portion 20 lies in a plane, illustrated at 30, which forms an angle, illustrated at 34, with a plane, illustrated at 32, in which the shank portion 16 lies, and the edge 24 faces away from plane 32. Thus, support portion 20 extends at the angle 34 relative to the shank portion 16.

The angle 34 is desirably selected so that the support portion 20 may follow the decline in the posterior part 28 of the upper tongue surface. Preferably, this angle 34 is between about 20 and 40 degrees. More preferably, this angle 34 is about 27 degrees.

In order to effectively reach into a depression, illustrated at 36, which runs rearwardly centrally of the tongue 12, the edge portion 22 is contoured over its length to have a relatively deep central portion, illustrated at 38. Thus, the central portion 38 has a depth, illustrated at 40, which is greater than depths, illustrated at 42, thereof toward the sides of the support portion 20.

The following dimensions of a suitable tongue cleaner are provided for exemplary purposes only and not for purposes of limitation. An example of a suitable tongue cleaner 10 has a length, illustrated at 44, of perhaps about 5 inches so that the edge 24 reaches the posterior of the tongue, a shank portion length, illustrated at 46, of perhaps about 3½ inches, and a thickness generally of perhaps about ¹⁄₁₆ inch. The edge portion 22 extends over a distance, illustrated at 48, cross-wise to the shank portion 16 of perhaps about 1½ inches. Distances 40 and 42 are perhaps about ¼ inch and ⅛ inch respectively. Angle 34 is perhaps about 27 degrees. The thickness of edge 24 may perhaps be about ¹⁄₆₄ inch. The width, illustrated at 50, of shank portion 16 may perhaps be about ⅜ inch. The distance, illustrated at 52, may perhaps be about ½ inch.

Although the invention has been described in detail herein, it should be understood that the invention can be embodied otherwise without departing from the principles thereof, and such other embodiments are meant to come within the scope of the present invention as defined by the appended claims.

What is claimed is:

1. A tongue cleaner comprising an article adapted for cleaning a person's tongue including means defining an elongate edge portion for engaging the tongue for scraping thereof, an elongate shank portion, a portion extending from said shank portion for supporting said edge portion for effecting engagement of said edge portion with a part of the upper surface of the tongue, and said edge portion extending generally cross-wise relative to said shank portion and being contoured over its length to have a relatively deep central portion thereby enabling said tongue cleaner to reach effectively into a depression running centrally of the tongue.

2. A tongue cleaner comprising an article adapted for scraping a tongue in a mouth including means defining an elongate edge portion for engaging the tongue for scraping thereof, a supporting portion, lying in a first downwardly sloping plane, for said edge portion, and an elongate shank portion, lying in a second plane which forms an angle with said first plane, wherein said edge portion extends generally cross-wise relative to said shank portion and is contoured over its length to have a relatively deep central portion.

3. A tongue cleaner according to claim 2 wherein said angle is between about 20 and 40 degrees.

4. A tongue cleaner according to claim 2 wherein said angle is about 27 degrees.

5. A tongue cleaner comprising an article adapted for scraping a tongue in a mouth including means defining an elongate edge portion for engaging the tongue for scraping thereof, a supporting portion, lying in a first downwardly sloping plane, for said edge portion, and an elongate shank portion, lying in a second plane which forms an angle with said first plane, wherein said edge portion extends generally cross-wise relative to said shank portion and is concave as viewed from said shank portion, and wherein said edge portion is contoured over its length to have a relatively deep central portion.

6. A tongue cleaner according to claim 5 wherein the tongue cleaner is sized to reach over the upper surface of a person's tongue including having a length of about 5 inches, a shank portion length of about 3½ inches, and the edge portion extending over a distance cross-wise to said shank portion of about 1½ inches.

7. A tongue cleaner comprising an article adapted for cleaning a person's tongue including means defining an elongate edge portion for engaging the tongue for scraping thereof, an elongate shank portion, and a relatively rigid portion for supporting said edge portion which support portion is skewed relative to said shank portion to slope downwardly for effecting engagement of said edge portion with a posterior part of the upper surface of the tongue, wherein said edge portion extends generally cross-wise relative to said shank portion and is contoured over its length to have a relatively deep central portion.

8. A tongue cleaner according to claim 7 wherein said support portion slopes at an angle of between about 20 and 40 degrees relative to said shank portion.

9. A tongue cleaner according to claim 7 wherein said support portion slopes at an angle of about 27 degrees relative to said shank portion.

10. A tongue cleaner comprising an article adapted for cleaning a person's tongue including means defining an elongate edge portion for engaging the tongue for scraping thereof, an elongate shank portion, and a relatively rigid portion for supporting said edge portion which support portion is skewed relative to said shank portion to slope downwardly for effecting engagement of said edge portion with a posterior part of the upper surface of the tongue 8 wherein said edge portion extends generally cross-wise relative to said shank portion and is concave as viewed from said shank portion, and wherein said edge portion is contoured over its length to have a relatively deep central portion.

11. A tongue cleaner according to claim 10 wherein said article is sized to have a length of about 5 inches, a shank portion length of about 3½ inches, and the edge portion extending over a distance cross-wise relative to said shank portion of about 1½ inches.

* * * * *